United States Patent [19]

Moossun

[11] 3,961,632
[45] June 8, 1976

[54] STOMACH INTUBATION AND CATHETER PLACEMENT SYSTEM

[76] Inventor: Mohamed H. Moossun, Box 237, R.R. 4, Elizabethtown, Ky. 42701

[22] Filed: Dec. 13, 1974

[21] Appl. No.: 532,735

[52] U.S. Cl. ............................... 128/347; 128/348; 128/DIG. 26
[51] Int. Cl.² .................. A61B 17/34; A61M 25/00
[58] Field of Search ........................... 128/347–351, 128/329, 6, 1.3, 2 M

[56] References Cited
UNITED STATES PATENTS

| | | | |
|---|---|---|---|
| 3,640,281 | 2/1972 | Robertson | 128/349 X |
| 3,656,486 | 4/1972 | Robertson | 128/349 R |
| 3,794,041 | 2/1974 | Frei et al. | 128/1.3 |

FOREIGN PATENTS OR APPLICATIONS

| | | | |
|---|---|---|---|
| 1,261,276 | 7/1965 | Germany | 128/6 |

*Primary Examiner*—Lawrence W. Trapp
*Attorney, Agent, or Firm*—Low & Matthews

[57] ABSTRACT

A trans-abdominal stomach catheter placement system involving an external nasogastric intubation device with a mobile distal end embracing magnetic determination of the device adjacent the abdominal wall and displacement of internal organs thereat to facilitate stomach perforation, of a catheter of the Foley type introduced by means of a needle and having additional external securement and traction means therefor.

6 Claims, 9 Drawing Figures

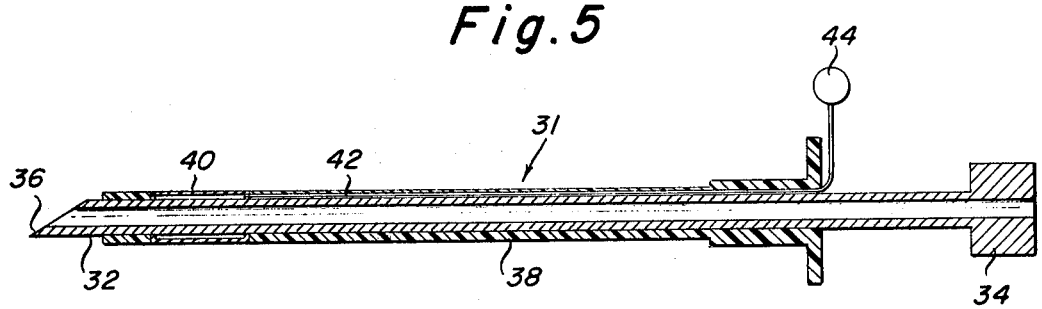
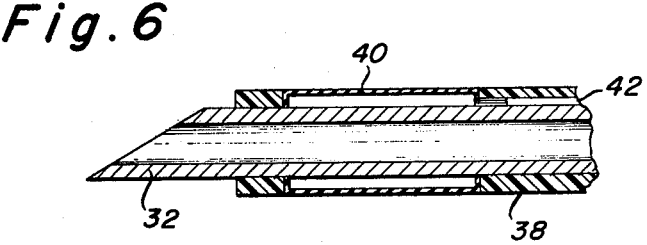
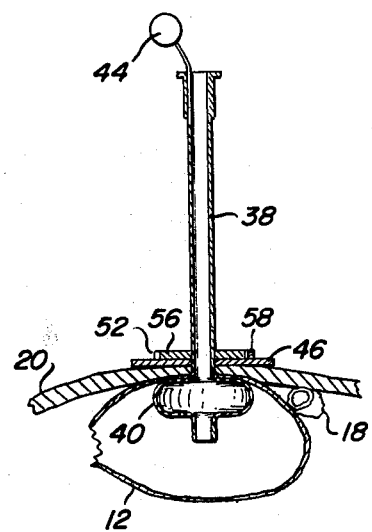
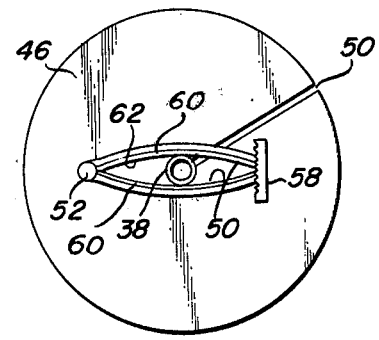
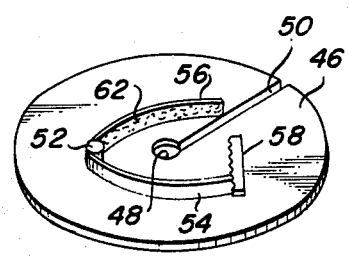

STOMACH INTUBATION AND CATHETER PLACEMENT SYSTEM

BACKGROUND OF THE INVENTION

In the art of inserting catheter and like devices into various portions of the anatomy, as in veins, urethra, etc, particular difficulty is encountered with respect to emplacing a catheter accurately and properly in the stomach area.

It is important in catheter placement that the external puncture from outside the abdomen engage and perforate the stomach wall, and not injure any nearby organs or any intestinal tract members which may lie or be temporarily disposed between the stomach and the abdomen exterior.

Further, after having once cut the flesh in inserting an abdominal catheter, it is important to secure the catheter in such manner that it will not readily become displaced and also maintain ready access thereto for repositioning, withdrawal, etc.

These concerns have manifested themselves in diverse magnetically guided devices for the vascular system as in Tillander U.S. Pat. No. 3,674,014, McCarthy U.S. Pat. No. 3,043,309 or Modny et al U.S. Pat. No. 2,863,458, or with respect to catheter securement in Peterson U.S. Pat. No. 3,490,457 or Reif U.S. Pat. No. 3,568,679.

None of these and similar presently known approaches teaches and cooperatively relate associated techniques relating to stomach intubation, abdominal wall puncture, catheter emplacement, and securement thereof as set forth in my invention hereinafter.

BRIEF DESCRIPTION OF THE INVENTION

In accordance with the present invention wherein a modified Foley catheter is inserted through the abdominal wall into the stomach and secured therein, in order to effectively dispose the stomach for ready and reliably located penetration by a trocar or the like, a novel magnetic intubation device and technique is employed to distend or advance the forward portion of the stomach wall into relatively close proximity to the exterior abdomen wall, and in so doing laterally displacing intestinal or other members which might lie therebetween, whereby damage to or cutting of such members is avoided in implanting the catheter.

Proper positioning of the catheter may be determined magnetically, and ultrasonic or other techniques may be employed to insure organs are properly displaced and that the magnet member has advanced the proper portion of the stomach into proximity to the abdomen exterior.

BRIEF DESCRIPTION OF THE DRAWINGS

The following specification should be taken in connection with the appended drawings in which:

FIG. 5 is a side sectional view of the catheter;

FIG. 6 is a fragmentary enlarged view of the terminal end thereof;

FIG. 7 is a diagrammatic side elevation of the catheter in place within the stomach and secured by the external clip of the invention;

FIG. 8 is a plan view of the external clip;

FIG. 9 is a perspective view of the external clip.

In accordance with my invention and in contrast to the magnetic plumb devices of the prior art, I provide an intubation device comprising a generally conventional flexible tube 10 which may be inserted in the usual manner as through the nasal passage to the esophagus to extend into stomach 12. The tube 10 is provided at its terminal end with a smooth closed and rounded tip 14 of cup-like configuration wherein the cup end is formed of ferrous metal or plastic which is coated or impregnated with ferrous particles.

Figure 1:
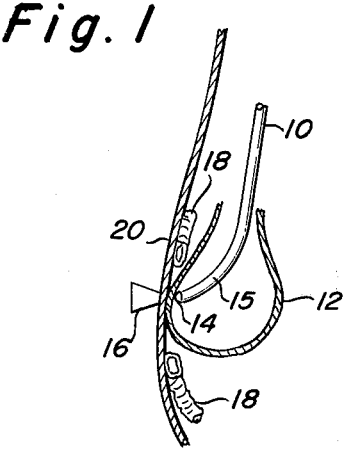
FIG. 1 is a diagrammatic view illustrating the intubation device inserted gastronomically and in conjunction with the external magnetic locator.

After the tip 14 of tube 10 has been introduced sufficiently into the stomach 12, an external locator device such as magnet 16 is manipulated to attract the tip 14 of the intubation device toward the abdominal wall, thereby distending the stomach and bodily shifting the forward portion thereof to the left as seen in FIG. 1. In so doing, any internal organs or members as diagrammatically indicated at 18 that may have been lying between the stomach 12 and the abdominal wall 20 will be displaced laterally or upwardly and downwardly, whereby the stomach will be in the closest possible proximity to the exterior of the body.

Before puncture is effected, however, it is preferable that a determination is made to insure that there is no obstruction or impediment existing between the stomach wall and body exterior. Such determination may be readily effected by a fluoroscope or by ultrasonic mapping techniques.

Figure 2:
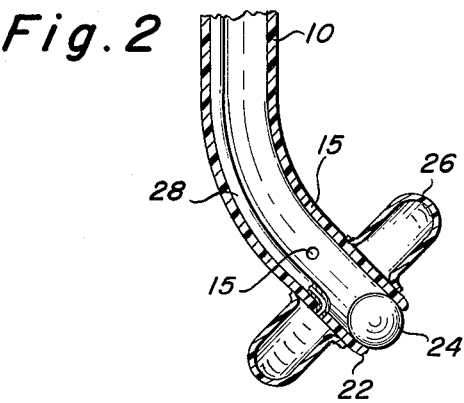
FIG. 2 is an enlarged fragmentary view showing the operative end of the magnetic intubation device.

In FIG. 2 I have shown a modification of the intubation tip which while more complex than the simpler form thereof in FIG. 1, possesses significant advantages.

Thus, in FIG. 2, in lieu of the cup-like end 14 at the end of the tube 10, the plastic tube is so shaped at its terminal end 22 so as to rollably retain therein a metallic ferrous ball member 24. Such a ball member 24 may roll readily over the inside of the stomach as the intubation device is inserted, especially as the ball and the stomach wall forwardly thereof is bodily attracted and translated forwardly by magnet 16.

To minimize locally high pressures which may be caused by the magnetic attraction against the relatively small ball, the tube 10 may also be provided at its lower terminal end with an inflatable annulus 26, shown inflated in FIG. 2, and supplied by an inserted or molded-in-situ air line 28 within tube 10. The annulus 26 enlarges the effective diameter of the tube end 22 and reduces the effective unit pressure per area on the stomach while a magnet 16 attracts the intubation device theretoward.

Figure 3:
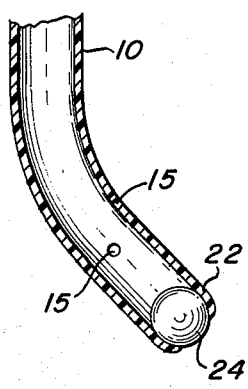
FIG. 3 is an enlarged fragmentary view of a modified form of the megnetic intubation device.

If these pressures are not unduly high, the annulus 26 may be omitted as seen in FIG. 3 and only the rolling magnetic ball employed.

Figure 4:
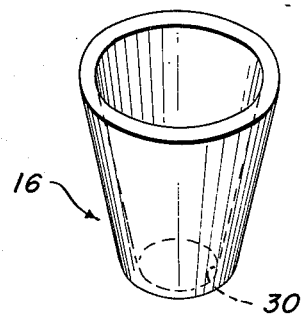
FIG. 4 is a perspective view enlarged of the external magnetic locator.

While any form of magnet will attract the magnetic intubation tip, it is preferable that the magnet 16 be annular with an aperture therethrough such as the frustoconical configuration thereof as seen in FIG. 4. The tapering wall of the magnet may be formed as desired of permanent magnet material such as ferrites or an Alnico permanent magnet as is well known in the art. The purpose of the annular configuration of magnet 16 is to permit the insertion therethrough of the abdomen puncturing tool in making the incision for the catheter. By having the aperture 30 in magnet 16, the tip 14 of the intubation device will be centered in the magnetic field and disposed behind an exposed area of flesh visible through the aperture 30, whereby it is certain the subsequent incision will not engage or injure other organs. If merely a single length of magnetic rod were employed, which of course is less desirable, the incision would of necessity have to be slightly laterally offset from the magnetic intubation tip and the possibility of damage to adjacent internal members increased.

A substantially Foley-type catheter 31 as seen in FIG. 5 is inserted through the abdominal wall 20 and of course once the catheter has been inserted, the intubation device which had been holding the stomach adjacent the body exterior can be removed. In its simplest form, the subject catheter includes a central steel needle 32 having an enlarged head 34 and terminating in an angled point 36. Surrounding the needle 32 is a closely fitting concentric tube 38 preferably of plastic and which includes adjacent its terminal end a layer of stretchable and resilient material or rubber 40 capable of lateral distension to form a cushioning annulus, as seen in FIG. 7. Such an inflating annulus is shown in U.S. Pat. No. 3,528,869 to Derenuik, for example.

Inflating air may be supplied to the annulus 40 to cause the same to distend to the extended position of FIG. 7, through a port as at 42 integrally formed or extruded with the plastic tube 38, wherein the airline 42 communicates with any convenient pressure source, such as a large hospital syringe or a detachable squeeze ball as at 44 diagramatically shown at the external end of the catheter.

Thereby, the catheter can be secured within the stomach 12 as seen in FIG. 7 upon expansion of annulus 40 thereby preventing withdrawal of tube 38.

It is necessary to secure the catheter externally of the abdomen so as to preclude inadvertent shifting thereof or untoward further introduction of the tube into the stomach while traction is applied to the tube and annulus 40 to pull the stomach wall against the abdominal wall until bleeding stops and scar tissue forms to aid adhesion therebetween. As bleeding is a significant medical complication of the disclosed technique, the pressure exerted by annulus 40 when traction is applied to 38 importantly forestalls this eventuality. To this end novel and effective securing means are provided in the form of locking disc 46, FIGS. 7-9. Disc 46 is provided with a central aperture 48 of a diameter sufficient to accommodate tube 38 freely but closely therein. The disc 46 is further preferably radially slotted at 50 to permit disc 46 to be slipped laterally onto tube 38 in placing the locking disc in position. The disc at the slot 50 will have its edges on the underside thereof gently rounded so as to prevent any bruising action on the skin therebeneath.

The disc 46 is preferably of plastic such as polystyrene or the like and includes an upstanding post 52 from which two resilient legs 54, 56 extend on either side of the central aperture 48. The disc 46 further includes an upstanding serrated latch member 58.

Each leg 54, 56 is preferably cushioned on its inner face with a layer of sponge or polyurethane material 60 and the confronting faces of the same are preferably faced with a pressure sensitive adhesive 62.

In this manner it will be seen that after initial positioning of the catheter and inflation annulus 40 within the stomach, the disc 46 may be inwardly laterally slid onto the disc 48, and thence axially advanced therealong to the desired degree of tightness against the skin, after which the legs 54, 56 are compressed toward each other and releasably latched against retaining serrations 58. The confronting tacky faces 62 of the legs will engage the tube 38, whereby the tube 38 is not merely frictionally held by a clamping action, but is readily restrained against any untoward or lateral movement by the tenacious adherence of the adhesively coated legs thereto.

The disc can of course be readily removed for repositioning, catheter removal or the like by flexibly detaching the flexible legs 54, 56 from the catheter tube 38.

While the tube 10 may be positioned and stomach 12 pierced as described, under certain conditions it may be advisable to inflat the stomach to a distended hollow cavity after the magnetic tip has been positioned as in FIG. 1. To this end, the tube 10 is provided with apertures 15 through which air may pass into the stomach pumped by a syringe or like means externally of the body. As is known in the art, inflation may be aided by obturating the stomach entrance with a second balloon annulus similar to that at 26 but located a substantial distance from the tube distal end, on the order of 12–18 inches.

What is claimed is:

1. A method of stomach manipulation for perforation thereof to receive a catheter comprising the steps of:
    intubating the stomach with an elongate flexible tubular member having a magnetically attractable tip thereon,
    magnetically attracting said tube tip from externally of the body thereby translating the stomach wall adjacent the tube lip laterally toward the body exterior and thereby displacing yieldable body members normally disposed therebetween, and
    perforating the body abdominal wall and the stomach therebehind in the immediate area of the magnetically attracted tip.

2. The method of claim 1 further including the step of inserting and securing a stomach catheter through the opening formed by the perforation.

3. An intubation system for implanting a catheter in a stomach comprising an elongated flexible tube for esophageal insertion into the stomach,
    a magnetically attractable tip on said tube, and,
    a magnet for manual positioning exteriorly of the body for attracting the magnetically attractable tube tip theretoward with a portion of the stomach wall therebetween, 4. The intubation system of claim 3 wherein said magnet comprises an annular magnet defining a central opening thereby to locate the attracted tip substantially at said opening.

5. The intubation system of claim 4 wherein said annular magnet is of frustoconical configuration.

6. A method of catheter emplacement comprising the steps of inserting a flexible tubular member having a magnetically attractable tip into the stomach,
    magnetically attracting the tip of such member from exteriorly of the body toward the abdominal wall thereby to translate the adjacent portion of the stomach theretoward,
    perforating the abdominal wall and the stomach at the attracted area thereof,
    inserting a catheter through the abdominal wall and into the stomach, and,
    securing the catheter in position by means of a frictional clip exteriorly of the body adjacent the abdominal wall.

* * * * *